(12) United States Patent
Usui

(10) Patent No.: US 6,386,265 B1
(45) Date of Patent: May 14, 2002

(54) METHOD OF AND APPARATUS FOR CASTING DENTAL PROSTHESIS

(75) Inventor: Masaki Usui, Kyoto (JP)

(73) Assignee: Denken Co., Ltd., Kyoto (JP)

( * ) Notice: Subject to any disclaimer, the term of this patent is extended or adjusted under 35 U.S.C. 154(b) by 0 days.

(21) Appl. No.: 09/444,205

(22) Filed: Nov. 22, 1999

(30) Foreign Application Priority Data

Dec. 14, 1998 (JP) ............................ 10-354062

(51) Int. Cl.$^7$ .................... B22D 13/00; B22D 27/15; B22D 46/00
(52) U.S. Cl. .................... 164/114; 164/116; 164/62; 164/457; 164/155.4
(58) Field of Search ................ 164/61, 62, 63, 164/116, 155.4, 151.2, 258, 259, 4.1, 451, 457, 114

(56) References Cited

U.S. PATENT DOCUMENTS

| | | | | |
|---|---|---|---|---|
| 4,627,482 A | * | 12/1986 | Waterstrat | 164/514 |
| 4,762,165 A | * | 8/1988 | Ogino et al. | 164/457 |
| 5,626,179 A | * | 5/1997 | Choudhurry et al. | 164/66.1 |

FOREIGN PATENT DOCUMENTS

| | | |
|---|---|---|
| JP | A-6-126422 | 5/1994 |
| JP | A-7-132364 | 5/1995 |

* cited by examiner

Primary Examiner—M. Alexandra Elve
Assistant Examiner—Len Tran
(74) Attorney, Agent, or Firm—Oliff & Berridge, PLC

(57) ABSTRACT

While rotating a chamber 10 with a crucible 18 for heating ingots 28 of metal and a mold 23 for receiving molten metal from the crucible 18 enclosed therein from a normal position to a reversed position, when an arrival of the chamber 10 at a preset reference position is detected by a rotary plate 36 and a position sensor 37, a pressure gas is introduced into the chamber 10 at a time point delayed from the reference position by a preset delay time. The delay time is preset so that the pressurize gas starts pressing the molten metal into a sprue runner 26 immediately after a mouth of the sprue runner 26 is completely closed by the molten metal poured from the crucible 18. Thus, the molten metal is promptly pressed through the sprue runner 26 into a cavity 27 of the mold 23 before it starts solidifying due to the contact with the mold 23 having a temperature lower than that of the molten metal.

2 Claims, 6 Drawing Sheets

AT NORMAL POSITION
(BEFORE ROTATION)

AT START OF
PRESSURIZING OPERATION

AT REVERSED POSITION

METHOD OF AND APPARATUS FOR CASTING DENTAL PROSTHESIS

The present invention relates to a method of manufacturing dental prostheses, such as an inlay, crown, base, implant, and upper part of implant, from precious metals or nonprecious metals by pressure casting. The present invention also relates to an apparatus for casting dental prostheses.

BACKGROUND OF THE INVENTION

If a person loses a part or whole of the teeth as a result of caries (tooth decay), periodontal disease or the like, the person suffers not only functional declination in speech and chewing and/or a change in the facial appearance, but also the health of the whole body is influenced badly thereby. It is therefore important to undergo a treatment as soon as possible to restore the missing tooth (or teeth). According to one of the known restoration methods, a metallic casting is put in place of the missing part of the teeth. Dental prostheses for restoring missing parts of teeth, however, cannot be mass-produced because there is a significant individual difference in the shape of teeth, and the size and shape of the missing part differs depending on the case. Therefore, it is necessary to manufacture a prosthesis having a particular shape depending on the case of each patient. Also, it is necessary to manufacture the prosthesis with a high degree of accuracy in order to provide a correct occlusion. Thus, in the field of dental casting, the lost wax process, which is known for providing a high degree of accuracy of casting, is generally used for obtaining castings that meet the above demands.

FIG. 6 is a flow chart showing the steps of dental casting according to the lost wax process. Referring to this FIG. 6, the steps of manufacturing a prosthesis used for dental treatment is described. At first, a dentist takes a negative impression model of the mouth and teeth around the object part of a patient (Step S1). A dental technician pours modeling material, such as gypsum, into the negative impression, and solidifies the material to produce a positive model (Step S2). The dental technician forms a casting model of the object part such as an inlay or crown using wax or resin on the positive model (Step S3). A sprue wire for forming a sprue runner is attached to an appropriate part of the casting model with wax or the like (Step S4). After that, the casting model is detached from the positive model, and the free end of the sprue wire is stabbed on a crucible former (Step S5).

FIG. 7 is a front view of a casting model mounted on a commonly used crucible former. The crucible former 60 has a conical base 61 formed at its center, and a hole 62 for inserting the sprue wire 64 is formed on the top of the conical base 61. The hole 62 is filled with softened wax and the free end of the sprue wire 64 (to which the casting model 63 is attached) is inserted in the soft wax. When the wax solidifies, the casting model 63 is fixed on the top of the conical base 61 with the sprue wire 64.

A metallic cylinder (not shown) is fit on the crucible former 60 so that the casting model 63 is surrounded by the cylinder, and investment material such as gypsum or phosphate is poured into the cylinder to conceal the casting model 63 (Step S6). After the investment material is solidified, the crucible former 60 is removed, and the investment material is heated (Step S7). By heating, the wax inside is burned off, leaving a cavity corresponding to the sprue wire 64 and the casting model 63. Thus, a mold is obtained.

Heating the mold to a preset temperature, molten metal is poured into a reservoir at the top of the mold, which is a conical depression having a shape corresponding to the conical base of the crucible former, and the molten metal flows into the cavity through the sprue runner (Step S8). After the poured metal has cooled down and solidified, the mold is broken to take out the casting inside (Step S9). Then, unnecessary parts such as fringe metals along the sprue runner is removed from the casting, and after-treatments such as sanding of the surface is carried out (Step S10). Thus, a prosthesis is completed.

For assisting molten metal to flow smoothly into the cavity in Step S8, one of the following three methods is generally used. The first is the centrifugal casting wherein the mold is revolved around an axis so that the molten metal is pressurized into the mold by the effect of the centrifugal force. The second is the pressure casting wherein the molten metal is at first poured into the reservoir under a vacuum, and the pressure is then increased so that the molten metal is forced into the cavity due to the pressure difference between the cavity and the outside (this process is referred to as "pressurizing operation" in this specification). The third is the vacuum casting wherein the molten metal poured into the reservoir is introduced into the cavity by evacuating the cavity from the other side.

Japanese Unexamined Patent Publication Nos. H06-126422 and H07-132364 disclose conventional casting apparatuses utilizing the pressure casting. The apparatus disclosed therein has a casting chamber in which a crucible and a mold are oppositely positioned across a horizontal axis so that the top of the crucible and the reservoir of the mold face each other. The casting chamber is rotatable about the horizontal axis to turn the posture of the casting chamber, or the relative position of the crucible and the mold, upside-down. At first the casting chamber is held in a position where the open top of the crucible is directed upwards, alloy ingots are put in the crucible, and the crucible is heated to melt the alloy. The mold located above the crucible is heated to a temperature of about 800–900 C (degrees Celsius), and the casting chamber is evacuated with a vacuum pump. At a preset timing when the pressure in the cavity inside the mold decreases adequately, the casting chamber is turned upside-down. The open top of the crucible is now directed downwards, and the molten metal in the crucible is poured into the reservoir of the mold. The molten metal closes the mouth of the sprue runner in an airtight manner. After that, the evacuation of the casting chamber is stopped, and the pressure in the casting chamber is increased by supplying gas such as pressurized air or inert gas, while the pressure in the cavity of the mold is maintained low. Due to the pressure difference, the molten metal is forced to flow through the sprue runner into the cavity of the mold. Thus, the pouring of the molten metal is completed.

In the above-described pressure casting process, if the pressurizing operation is started before an appropriate amount of molten metal is poured in the reservoir, the gas used for increasing the pressure in the chamber intrudes into the cavity, which results in defects in the casting. For preventing this, it is desirable to start the pressurizing operation after an adequate amount of molten metal is poured in the reservoir.

When an alloy having a high melting point (usually over 1000 C), such as nickel-chromium alloy or cobalt-chromium alloy, is used as the casting material, the following problem must be considered. Even when a mold is made of an investment material durable to high temperature casting (e.g. material of the phosphate group), the highest allowable temperature is about 900 C. This means that, in casting, the temperature of the mold is normally lower than the melting point of the molten metal. Therefore, it is probable that the molten metal solidifies before the pressurizing operation starts since the temperature of the molten metal decreases rapidly after the molten metal is poured into the mold. Even if the molten metal does not solidify, casting defects due to an inadequate pouring is likely to occur since a lowered fluidity of the molten metal prevents it from flowing smoothly.

When the temperature of the molten metal is set higher, the time required for the solidification of the molten metal poured into the mold becomes longer, and the casting workability is enhanced. When, however, the temperature is too high, the molten metal reacts with the investment material of the mold, and the surface of the casting becomes rough. As a result, the time required for the after-treatments such as sanding increases, and the working efficiency deteriorates. Also, too high a temperature of the molten metal often causes undesirable effects on the properties such as the hardness or toughness of the casted object.

SUMMARY OF THE INVENTION

For addressing the above-described problems, an object of the present invention is to propose a pressure casting method which provides high casting workability even when a metal having a high melting point is used. Also, the present invention proposes an apparatus for casting a dental prosthesis according to the method of the present invention.

Thus, the present invention proposes a method of casting a dental prosthesis by pressure casting using an airtight chamber containing a crucible and a mold with an open top of the crucible and a mouth of a sprue runner of the mold facing each other across a rotating axis of the airtight chamber, the method including the steps of:

putting the airtight chamber at a position where the crucible with a quantity of metallic material is at the bottom and the mold is at the top;

heating the crucible to melt the quantity of metallic material to produce a quantity of molten metal; and rotating the airtight chamber around the rotating axis until the airtight chamber is substantially reversed, which is characterized in that:

the pressure in the airtight chamber is maintained low until a preset time point before the rotation of the airtight chamber is completed, and a pressure gas is supplied in the airtight chamber at the preset time point.

Also, the present invention proposes an apparatus for casting a dental prosthesis by pressure casting, including:

an airtight chamber containing a crucible and a mold with an open top of the crucible and a mouth of a sprue runner of the mold facing each other across a rotating axis of the airtight chamber;

a heater for heating the crucible;

a rotating mechanism for rotating the airtight chamber around the rotating axis;

a position sensor for detecting a preset angular position of the airtight chamber between a normal position where the crucible is at the bottom and the mold is at the top and a reversed position where the mold is at the bottom and the crucible is at the top;

a delay time storing means for storing an externally given delay time; and a pressure controller for maintaining a low pressure in the airtight chamber until a second time point which is the delay time after a first time point when the position sensor detects the preset angular position of the airtight chamber and for supplying a pressure gas in the airtight chamber at the second time point.

In conventional pressure casting methods, the pressure gas is supplied into the chamber when or after the chamber arrives at the reversed position. In the pressure casting method according to the present invention, on the other hand, the pressure gas is supplied before the rotation of the airtight chamber is completed. In other word, the gas is supplied during the rotation of the chamber at a time point when the chamber arrives at an angular position preset between the normal position and the reversed position.

In general, a high melting point metal has high fluidity (or low viscosity) in the molten state. Therefore, when the chamber comes to an angular position of about 120 degrees from the normal position (or 60 degrees to the reversed position), the molten metal starts flowing out of the inclined crucible and is poured into the reservoir of the mold. When the molten metal completely closes the mouth of the sprue runner, the pressure gas is supplied into the chamber. As the pressure increases, the molten metal is pressed through the sprue runner into the cavity inside the mold due to the pressure difference between the cavity and the outside of the mold. The further the chamber rotates, the more the molten metal is poured into the mold. Thus, the molten metal is continuously supplied into the sprue runner following to the molten metal already existing in the sprue runner. Since the molten metal poured into the mold is promptly pressed into the cavity, the molten metal is prevented from solidifying at the mouth of or in the sprue runner. Since the pressurizing operation is started after the molten metal completely closed the mouth of the sprue runner, the pressure gas is prevented from intruding into the sprue runner.

The fluidity of a molten metal depends on the kind of the metal, temperature of the metal, and other factors. Therefore, it is preferable to determine an appropriate timing for starting the pressurizing operation according to the above factors. Thus, the apparatus according to the present invention is provided with the means for storing the delay time for the operator to determine an appropriate delay time according to the above factors, whereby the casting workability is assuredly maintained at high level.

As described above, by using a pressure casting method or apparatus according to the present invention, the molten metal poured into the reservoir of the mold smoothly flows through the sprue runner into the cavity since the pressurizing operation is started at an appropriate timing before the molten metal solidifies. Therefore, casting defects due to inadequate casting are prevented, and the manufacturing efficiency of dental prosthesis is improved.

BRIEF DESCRIPTION OF THE DRAWINGS

A preferred embodiment will be described referring to the attached drawing, where.

DETAILED DESCRIPTION OF A PREFERRED EMBODIMENT

Figure 1:
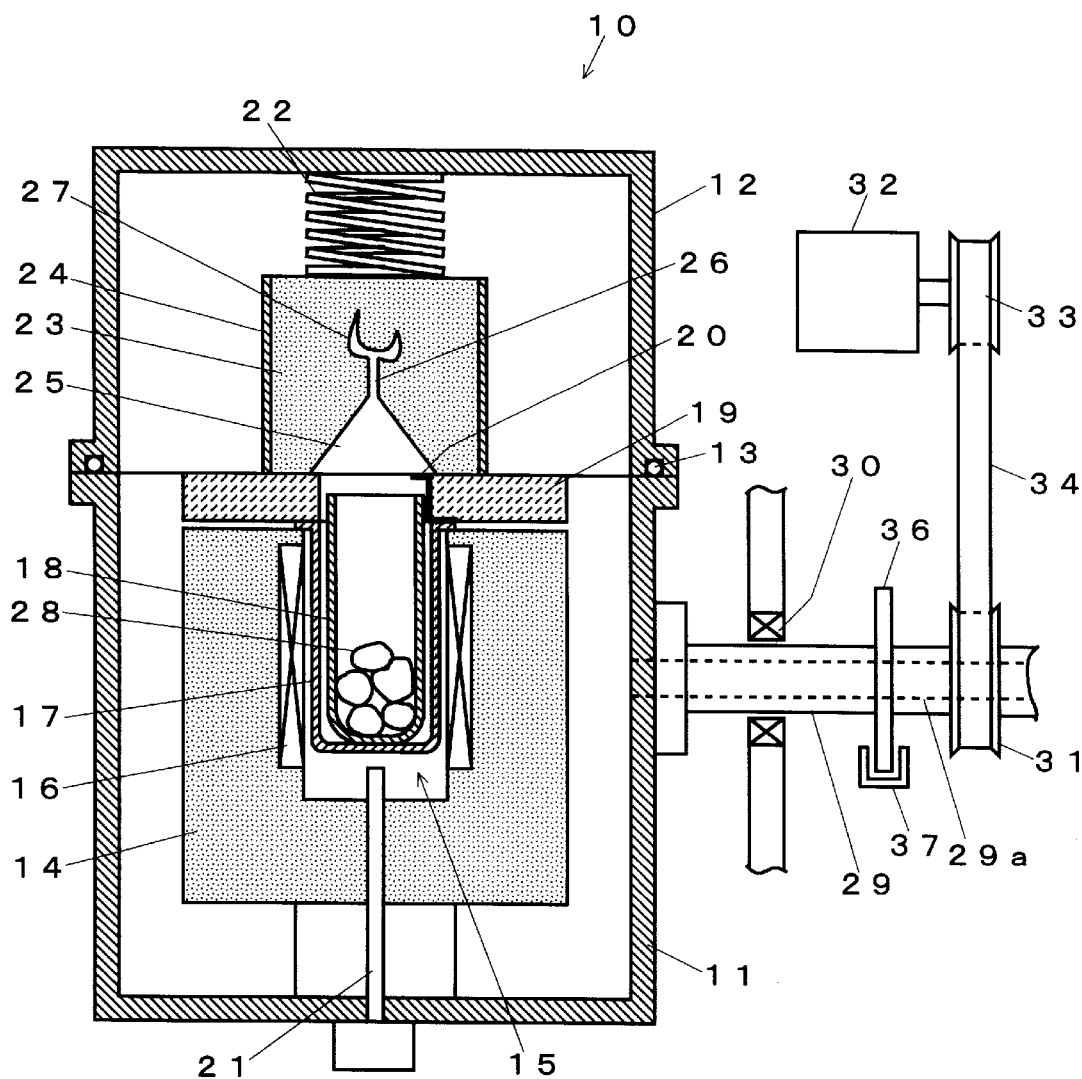
FIG. 1 shows a main part of a pressure casting apparatus as an embodiment of the present invention.

FIG. 1 shows a vertical section of a pressure casting apparatus according to the present invention in which a reversible chamber 10 is provided. The chamber 10 in FIG. 1 is in the normal position.

The chamber 10 has a container 11 and a cover 12, which are made of metal and coupled together by a hinge (not shown). An O ring 13 is provided at the lower end of the cover 12 for sealing the gap between the container 11 and the cover 12. Thus, when the cover 11 is locked on the top of the container 12 by a lock device (not shown), the inner space of the chamber 10 is sealed in an airtight manner. The chamber 10 is designed to bear an inner pressure of about 1 MPa or higher (in this specification, the pressure is represented in terms of pressure difference from the atmospheric pressure). In the container 11 is provided a support base 14 made of an insulating material. The support base 14 has a cylindrical cavity 15 extending downwards from its top, and a heater 16 is provided in the inner side wall of the cavity 15. A wire heater made of platinum alloy or ceramic heater made of silicon carbide may be used as the heater 16.

In the cavity 15 of the support base 14 is placed a retort 17 made of ceramic and having an open top and a closed bottom, and a crucible 18 is removably placed in the retort 17. The retort 17 has a flange extending outwards at its top, and an upper support member 19 made of refractory material and having an opening is provided so that it presses the flange from above. Thus, the retort 17 never falls from the cavity 15 even when the chamber 10 is turned upside-down (or reversed). The upper support member 19 is provided with a stopper 20 that can be pulled out of or pushed into the circumferential wall of the opening of the upper support member 19. When the chamber 10 is turned, the stopper 20 is pulled out, and the open top of the crucible 18 is stopped by the stopper 20. In the space between the bottom of the cavity 15 of the support base 14 and the bottom of the retort 17 is provided a thermocouple 21 for detecting the temperature of the crucible 18.

Figure 6:
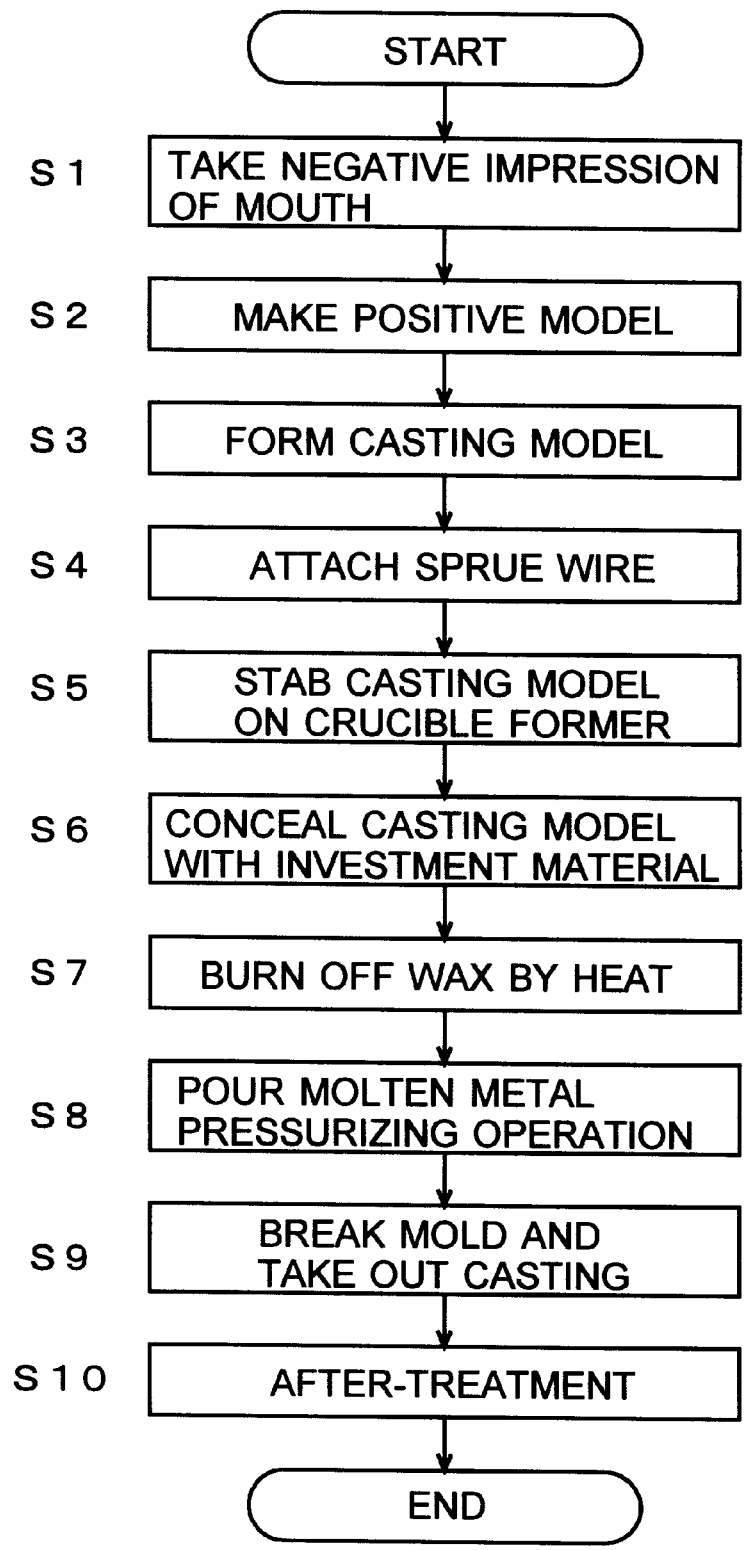
FIG. 6 is a flow chart showing steps of casting a dental prosthesis by the lost wax process.
Figure 7:
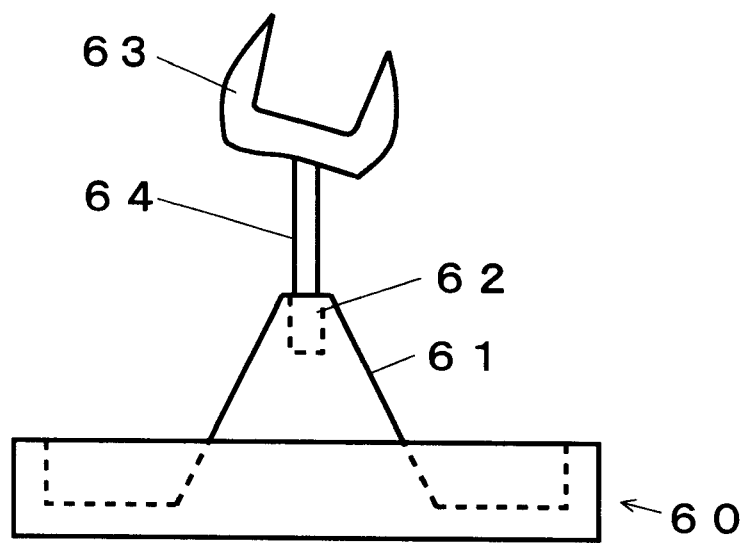
FIG. 7 is a front view of a casting model mounted on a commonly used crucible former.

A coil spring 22 is attached to the back of the top of the cover 12 of the chamber 10, and a mold 23 with a conical reservoir 25 directed downwards is placed between the coil spring 22 and the upper support member 19. A metallic cylinder 24 is fit on the side of the mold 23. The coil spring 22 presses the mold 23 from above, so that the lower end of the mold 23 tightly contacts the top of the upper support member 19. Plural cut paths (not shown) are formed on the lower end of the mold 23 and the cylinder 24 for allowing communication between the reservoir 25 and the inner space of the chamber 10. A sprue runner 26 having a mouth at the apex of the conical reservoir 25 connects the reservoir 25 and a cavity 27 formed in the mold 23. The sprue runner 26 and the cavity 27 are formed in the mold 23 by, for example, a lost wax process utilizing steps S1–S7 of FIG. 6.

A horizontal rotating shaft 29 is fixed to a side of the container 11 of the chamber 10, and is rotatably held by a bearing 30. The rotating shaft 29 is driven by a mechanism including a motor 32, a first pulley 33 fixed to the shaft of the motor 32, a second pulley 31 fixed to the rotating shaft 29, and a timing belt 34 for connecting the two pulleys 31 and 33. A rotary plate 36 fixed to the rotating shaft 29 and a photo sensor 37 placed near the rotary plate 36 constitute a position sensor for detecting the angular position of the chamber 10. The apparatus of the present embodiment uses two photo sensors, a normal position sensor 37a and a reversed position sensor 37b, which will be described later, though FIG. 1 shows only one photo sensor 37. The rotary plate 36 may be fixed to the shaft of the motor 32, and the photo sensors may be placed accordingly. The rotating shaft 29 is provided with a gas passage 29a inside. The gas passage 29a connects the inside of the chamber 10 and a vacuum pump or gas introduction valve, which will be described later.

Figure 2:
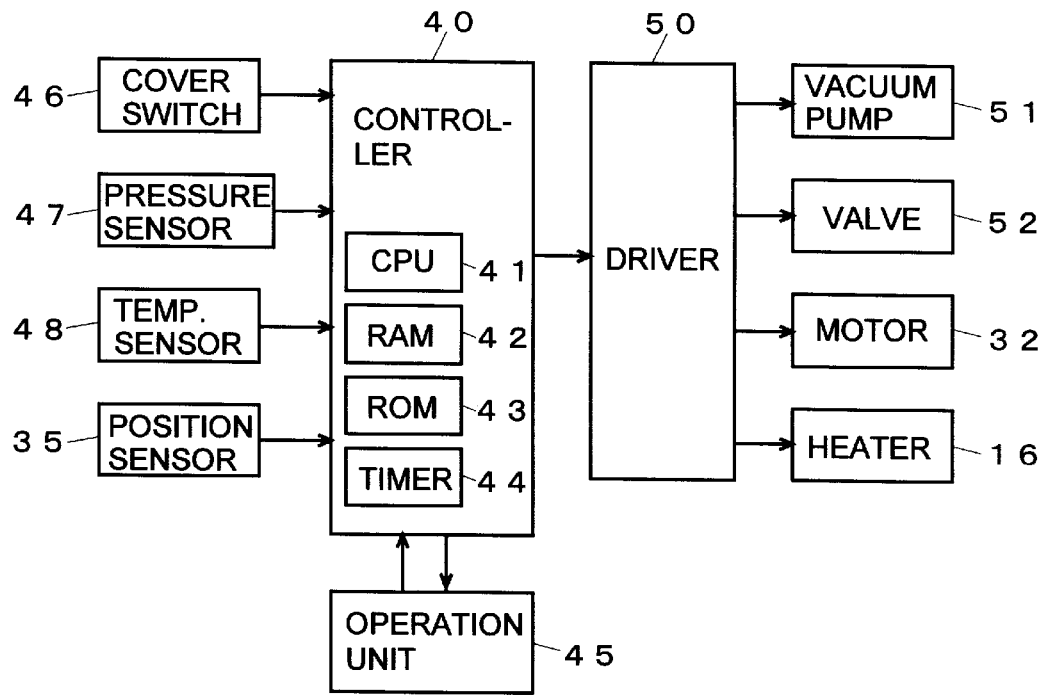
FIG. 2 is a block diagram of an electrical system of the apparatus of the embodiment.

The electrical system of the present embodiment is described referring to FIG. 2. The electrical system includes a controller 40, the main part of which is constituted by a microcomputer (or microcomputers) including a central processing unit (CPU) 41, random access memory (RAM) 42, read only memory (ROM) 43, timer 44, etc. The controller 40 receives detection signals from devices including: a cover switch 46 for detecting the state (open or close) of the cover 11 of the chamber 10; a pressure sensor 47 for detecting the pressure in the chamber 10; a temperature sensor, including the thermocouple 21, for detecting the temperature of the crucible 18; and a position sensor 35, including the rotary plate 36, for detecting the normal position, reversed position and reference position of the chamber 10 as described later. The controller 40 is connected to an operation unit 45 having operation buttons and display devices. When the user (e.g. dental technician) operates the operation unit 45, operation signals are sent to the control unit 40. The controller 40 is also connected to a driver unit 50 for controlling operations of a vacuum pump 51, gas introduction valve 52, motor 32 and heater 16. The vacuum pump 51 is operative to discharge air form the chamber 10 through the gas passage 29a. The gas introduction valve 52 is operative to introduce air, argon or other inert gas into the chamber 10 through the gas passage 29a. For quickly increasing the pressure in the chamber 10, the gas introduction valve 52 is connected to a gas cylinder from which content gas (pressurized air or inert gas) is supplied at a pressure of about 0.35 MPa. The motor 32 is operative to rotate the chamber 10, and the heater 16 is operative to heat the crucible 18, as described above.

Figure 3:
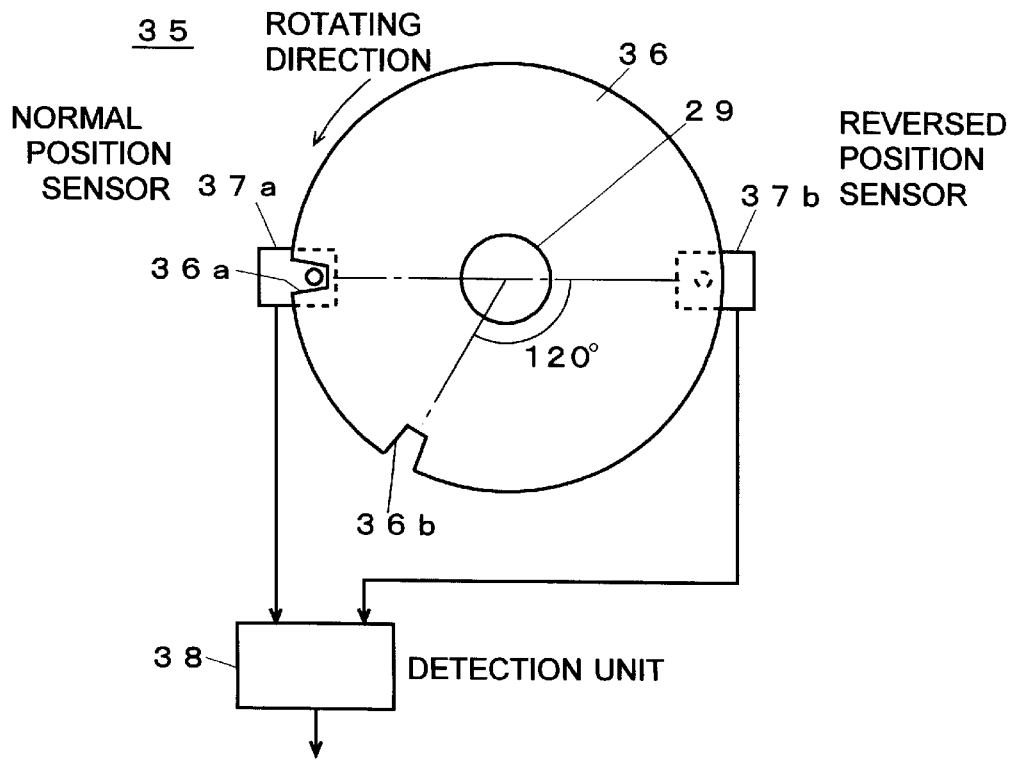
FIG. 3 schematically shows the constitution of a position sensor of the embodiment.

The constitution of the position sensor 35 is described referring to FIG. 3. The rotary plate 36 is provided with two slits 36a and 36b in its circumference. The second slit 36b is formed at a position in advance of the position of first slit 36a by 60 degrees in the rotating direction of the chamber 10. The normal position sensor 37a is located at a position where the first slit 36a comes when the chamber 10 is in the normal position, and the reversed position sensor 37b is placed in opposition to the normal position sensor 37a across the rotating shaft 29. Each of the two sensors 37a and 37b is constituted such that a photo emitter and a photo detector are placed in opposition to each other across the circumference of the rotary plate 36, as shown in FIG. 1. Light emitted from the photo emitter is detected by the photo detector when one of the slits 36a and 36b passes by the sensor 37a or 37b.

The position sensor 35 includes a detection unit 38 that detects the normal position, reversed position and reference position of the chamber 10 based on detection signals from the two sensors 37a and 37b as follows. In the following description, it is supposed that the reference position is preset at 120 degrees from the normal position. First, the detection unit 38 determines that the chamber 10 is in the normal position when it receives a detection signal from the normal position sensor 37a. Then, the rotation of the chamber 10 is started from the normal position. During the rotation of the chamber 10, the second slit 36b arrives at the reversed position sensor 37b and the reversed position sensor 37b sends a detection signal to the detection unit 38 when the chamber rotates 120 degrees. On receiving a detection signal from the reversed position sensor 37b for the first time from the start of the rotation of the chamber 10, the detection unit 38 determines that the chamber 10 is at the reference position. As the chamber 10 further rotates and, when the first slit 36a arrives at the reversed position sensor 37b, the reversed position sensor 37b sends a detection signal to the detection unit 38 again. On receiving the second detection signal from the reversed position sensor 37b, the detection unit 38 determines that the chamber 10 is at the reversed position.

In the apparatus of the present embodiment, the user can set various parameters relating to casting conditions by operating the buttons of the operation unit 45. The parameters include: heating temperature of the metal; melting time of the metal; and timing of breaking the vacuum and starting the pressurizing operation in the chamber 10 (the timing is referred to as "pressurizing timing"). In the present embodiment, the user can determine the pressurizing timing by selecting one of values from −0.5 to +0.5 [second] with steps of 0.1 [second], where zero corresponds to the time point at which the chamber 10 is at the reversed position. When the pressurizing operation is to be started before the chamber 10 arrives at the reversed position, one of the negative timing values is selected, and vice versa.

Figure 4:
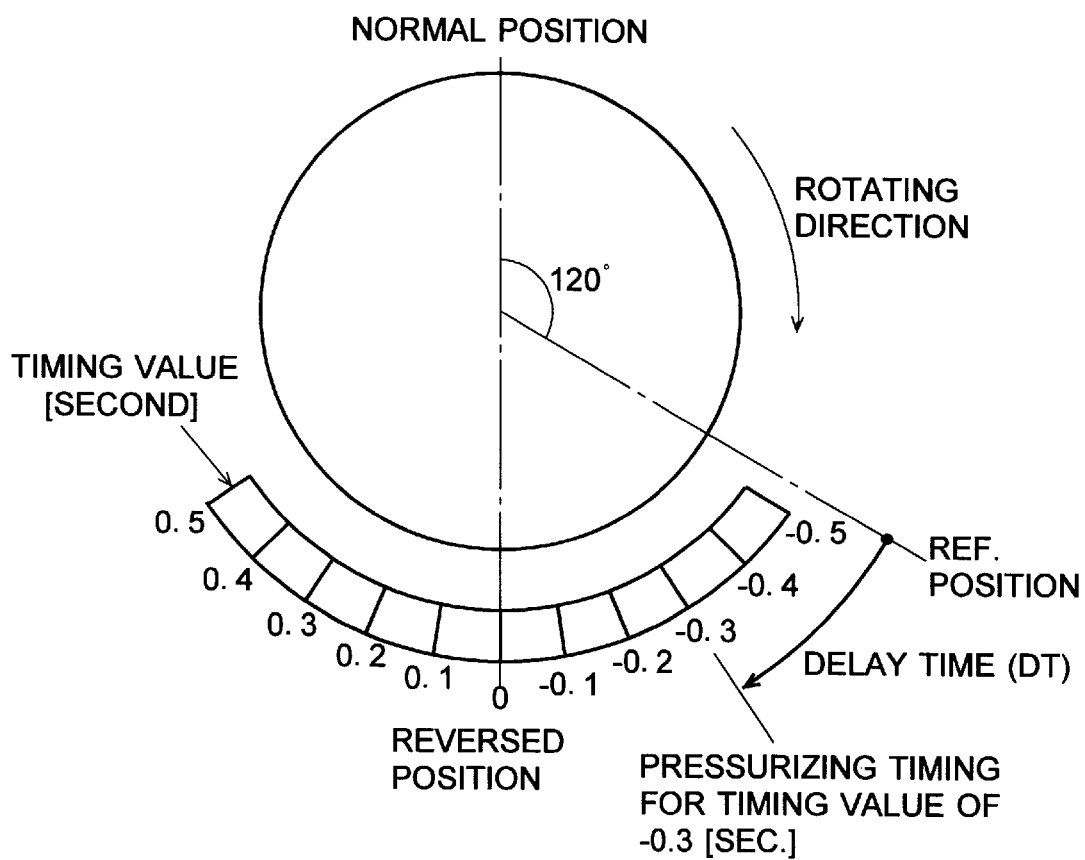
FIG. 4 shows an example of the relation between the angular position of the chamber and the timing of starting the pressurizing operation.

In the apparatus of the present embodiment, a synchronous motor is used as the motor 32, and the speed of the motor 32 is maintained constant during the rotation of the chamber 10. The constant speed is preset so that the time required for the chamber 10 to rotate from the normal position to the reversed position is about one second or slightly longer. Thus, the time required for the chamber 10 to rotate from the reference position to the reversed position can be calculated (this time is referred to as "reference time period"). An example of the relation between the angular positions of the chamber 10 and the timing values within the range of −0.5 to +0.5 [second] is shown in FIG. 4. The chamber 10 never actually reaches the angular positions corresponding to positive timing values. These angular positions are imaginary positions which the chamber 10 would reach if the chamber 10 were not stopped at the reversed position. As shown in FIG. 4, the pressurizing timing can be represented by a delay time DT corresponding to an angular displacement from the reference position. Thus, when a timing value is selected from the preset values of −0.5 to +0.5 [second], the controller 40 calculates the delay time DT by adding the selected timing value and the reference time period, and opens the gas introduction valve 52 when the delay time lapses after the chamber 10 passes the reference position. This process is performed by executing a program on the CPU 41, which is stored beforehand in the ROM 43.

Figure 5A:
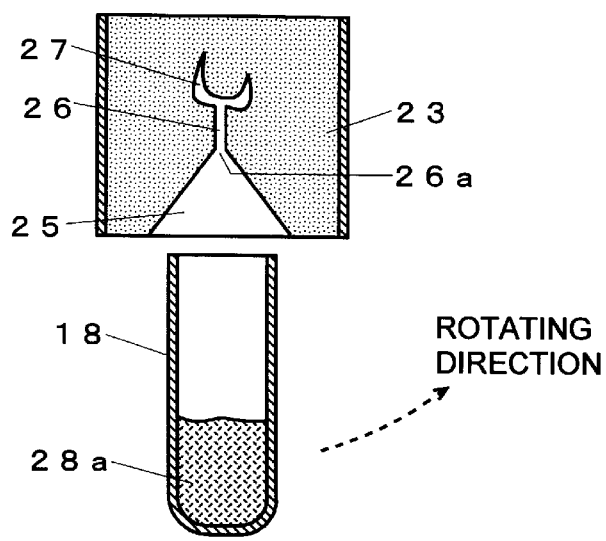
FIGS. 5A–5C show the motion of the crucible, the mold and the molten metal during the rotation of the chamber.
Figure 5B:
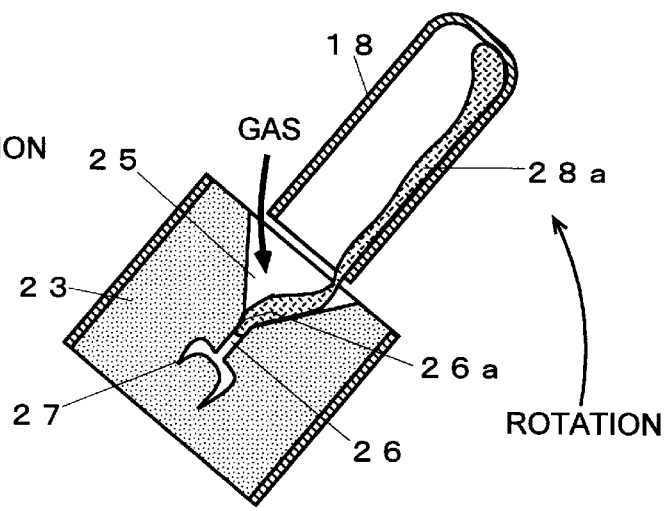
Figure 5C:
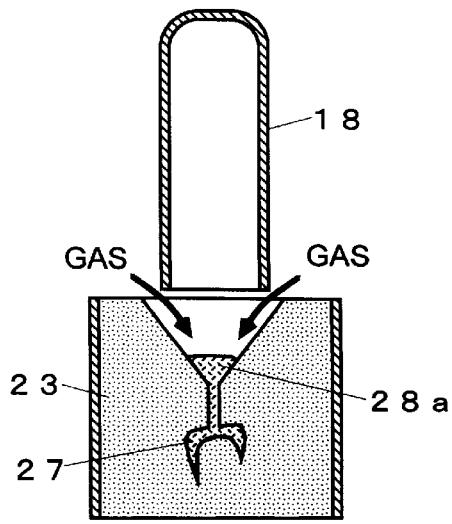

Casting operation of the apparatus of the present embodiment is described referring to FIGS. 5A–5C. First, the user operates the operation unit 45 and determines the parameters of casting condition, including the timing value corresponding to a desired pressurizing timing. It is possible, in an alternative way, to prepare several sets of parameters and store them in the RAM 42 beforehand. When the user operates the casting apparatus, the user can select one of the parameter sets, which facilitates the parameter setting operation. Suppose here that the timing value selected by the user is −0.3 [second].

Then, the user puts metal ingots 28 in the crucible 18 set in the retort 17, and gives a start heating command to the controller 40 through the operation unit 45. The controller 40 commands the driver unit 50 to start power supply to the heater 16. The crucible 18 is heated to above the melting point of the metal (the temperature is about 1000 C for precious metals or about 1400 C for nonprecious metals). Thus, the ingots 28 melt down, and molten metal is obtained.

The user heats the mold 23 in another furnace to 800–900 C, and sets the heated mold 23 over the crucible after the metal melts. When the cover 12 is locked on the top of the container 11, the cover switch 46 sends a cover locking signal to the controller 40. The mold 23 is now strongly pressed downwards by the coil spring 22, and the mouth 26a of the mold 23 faces the open top of the crucible 18 as shown in FIG. 5A.

When the user gives a start casting command to the controller 40, the controller 40 commands the driver unit 50 to close the gas introduction valve 52 and energize the vacuum pump 51. Thus, air in the chamber 10 is discharged through the gas passage 29a to the outside, so that the pressure in the chamber 10 decreases. During this evacuating operation, the temperature of the crucible 18 is maintained at above the melting point of the metal. The controller 40 monitors the pressure in the chamber 10 with the pressure sensor 47. When the pressure decreases to a preset level (−0.1 MPa, for example), the controller 40 commands the driver unit 50 to energize the motor 32. Thus, the chamber 10 starts rotating from the normal position to the reversed position. If the molten metal 28a in the crucible 18 has adequately high fluidity, the molten metal 28a flows out of the inclined crucible 18 and is poured into the reservoir 25 of the mold 23 by the time point when the chamber 10 arrives at the reference position.

When the chamber 10 rotates 120 degrees from the normal position, the rotation sensor 35 generates a detection signal indicating the arrival of the chamber 10 at the reference position. On receiving the detection signal, the controller 40 starts measuring time (lapse time). When the lapse time attains a delay time DT corresponding to the selected timing value of −0.3 [second], the controller 40 commands the driver unit 50 to stop the vacuum pump 51 and opening the gas introduction valve 52. Then, pressurized gas (air or inert gas) floods through the gas passage 29a into the chamber 10. The gas further flows through the gap between the open top of the crucible 18 and the mold 23 into the reservoir 25. Thus, as shown in FIG. 5B, the gas presses the molten metal 28a in the reservoir 25 from above immediately after the mouth 26a is completely closed by the molten metal 28a poured from the crucible 18. Since the inner space of the chamber 10 is evacuated until the gas is introduced, the inside of the cavity 27 capped by the molten metal 28a is in vacuum. Therefore, the molten metal 28a at the mouth 26a is pressed through the sprue runner 26 into the cavity 27 due to the pressure difference between the cavity 27 and outside of the mold 23. Meanwhile, as the chamber 10 further rotates, the crucible 18 comes closer to an upright position (reversed position), so that the molten metal 28a is supplied continuously from the crucible 18 into the mold 23, preventing intrusion of the gas into the sprue runner 26. Thus, since the molten metal 28a poured into the crucible 25 is pressed into the cavity 27 before it cools down and loses its fluidity, the casting workability is assuredly maintained at high level.

When the chamber 10 arrives at the reversed position as shown in FIG. 5C, the rotation sensor 35 generates a detection signal indicating it. On receiving the detection signal, the controller 40 commands the driver unit 50 to stop the motor 32 and, after a preset time period, to stop the power supply to the heater 16. The delay time for the heater stop is determined taking account of the system design that the latest pressurizing timing is 0.5 second after the chamber 10 arrives at the reversed position. When the power supply to the heater 16 is stopped, the inside of the chamber 10 cools down naturally, and the molten metal 28a filled in the cavity 27 of the mold 23 starts solidifying. After a preset casting time (several tens of seconds or several minutes, for example) lapses, the controller 40 commands the driver unit 50 to drive the motor 32 so that the chamber 10 is rotated from the reversed position back to the normal position. When the controller 40 detects that the chamber 10 has arrived at the normal position from the detection signal of the rotation sensor 35, the motor 32 is stopped. Thus, the casting operation is completed. In the above-described process, the time period of retaining the chamber 10 at the reversed position may be changed depending on the melting point of the metal. When the melting point of the metal is high, the retention time can be relatively short since the solidification proceeds promptly. When the melting point of the metal is low, on the contrary, it is necessary to set the retention time relatively long.

After that, the operator opens the cover 12 of the chamber 10, and takes out the mold 23. After the mold 23 cools down adequately, the operator pulls the mold 23 out of the metallic cylinder 24, and takes out the cast metal by breaking the mold 23.

In the above-described apparatus, when a metal having a high melting point is used as the casting material, it is preferable to start the pressurizing operation immediately after the mouth 26a is completely closed by the molten metal 28a. According to an experiment by the inventor, when the timing value is selected within the range of −0.4 to −0.2 [second], the pouring is successfully completed without causing casting defects. In the case where a low melting point metal having low fluidity in the molten state is used as the casting material, the casting defects tend to arise if the pressurizing operation is started too early, since the mouth 26a is not closed by the molten metal 28a. In such a case, casting defects can be prevented by setting the timing value within the range of +0.1 to +0.5 [second]. Thus, in the apparatus of the present embodiment, the pressurizing timing should be appropriately set depending on the kind of the casting material.

The above-described embodiment is a mere example of the present invention, which can be modified within the true spirit and scope of the invention.

What is claimed is:

1. A method of casting a dental prosthesis by pressure casting using an airtight chamber containing a crucible and a mold with an open top of the crucible and a mouth of a sprue runner of the mold facing each other across a rotating axis of the airtight chamber, the method comprising steps of:

putting the airtight chamber at a position where the crucible with a quantity of metallic material is at a bottom and the mold is at a top;

heating the crucible to melt the quantity of metallic material to produce a quantity of molten metal; and rotating the airtight chamber around the rotating axis until the airtight chamber is substantially reversed, which is characterized in that:

the pressure in the airtight chamber is maintained low until a preset time point before the rotation of the airtight chamber is completed, and a pressure gas is supplied in the airtight chamber at the preset time point.

2. An apparatus for casting a dental prosthesis by pressure casting, comprising:

an airtight chamber containing a crucible and a mold with an open top of the crucible and a mouth of a sprue runner of the mold facing each other across a rotating axis of the airtight chamber;

a heater for heating the crucible;

a rotating mechanism for rotating the airtight chamber around the rotating axis;

a position sensor for detecting a preset angular position of the airtight chamber between a normal position where the crucible is at a bottom and the mold is at a top and a reversed position where the mold is at the bottom and the crucible is at the top;

a delay time storing means for storing an externally given delay time; and a pressure controller for maintaining a low pressure in the airtight chamber until a second time point which is the delay time after a first time point when the position sensor detects the preset angular position of the airtight chamber and for supplying a pressure gas in the airtight chamber at the second time point.

\* \* \* \* \*